(12) United States Patent
Obenchain et al.

(10) Patent No.: US 7,749,251 B2
(45) Date of Patent: Jul. 6, 2010

(54) METHOD AND APPARATUS FOR STABILIZATION OF FACET JOINT

(75) Inventors: Theodore G. Obenchain, Escondido, CA (US); Laurence M. McKinley, Escondido, CA (US)

(73) Assignee: Aeolin, LLC, Escondido, CA (US)

( * ) Notice: Subject to any disclaimer, the term of this patent is extended or adjusted under 35 U.S.C. 154(b) by 1098 days.

(21) Appl. No.: 10/462,308

(22) Filed: Jun. 13, 2003

(65) Prior Publication Data

US 2004/0254575 A1 Dec. 16, 2004

(51) Int. Cl.
*A61B 17/70* (2006.01)
*A61B 17/88* (2006.01)

(52) U.S. Cl. .................................. 606/247; 606/86 A

(58) Field of Classification Search .................. 606/73, 606/104, 246, 247, 306, 311, 317, 99, 86 A; 81/57.11–57.14; 433/103, 112, 114, 147
See application file for complete search history.

(56) References Cited

U.S. PATENT DOCUMENTS

| | | | |
|---|---|---|---|
| 984,756 A | | 2/1911 | Frisch |
| 2,042,376 A | * | 5/1936 | Balga .......................... 279/89 |
| 2,248,054 A | * | 7/1941 | Becker ........................ 81/457 |
| 2,406,952 A | * | 9/1946 | Josepho ...................... 81/452 |
| 3,696,694 A | * | 10/1972 | Boro ......................... 81/57.27 |
| 3,752,161 A | * | 8/1973 | Bent ........................... 606/184 |
| 4,056,762 A | * | 11/1977 | Schadlich .................... 318/484 |
| 4,586,497 A | * | 5/1986 | Dapra et al. ................... 606/80 |
| 4,743,260 A | | 5/1988 | Burton |
| 4,852,554 A | * | 8/1989 | Alten .......................... 128/897 |
| 4,936,313 A | * | 6/1990 | Burkhardt et al. ........... 600/564 |
| 4,990,148 A | * | 2/1991 | Worrick, III et al. .......... 606/83 |
| 5,015,255 A | | 5/1991 | Kuslich |
| 5,026,375 A | * | 6/1991 | Linovitz et al. ............... 606/79 |
| 5,139,499 A | * | 8/1992 | Small et al. ................... 606/73 |
| 5,282,863 A | | 2/1994 | Burton |
| 5,312,407 A | * | 5/1994 | Carter ......................... 606/79 |
| 5,385,570 A | * | 1/1995 | Chin et al. ................... 606/170 |
| 5,391,170 A | | 2/1995 | McGuire et al. |

(Continued)

OTHER PUBLICATIONS

International Search Report date Oct. 27, 2003 for International Application No. PCT/US03/18672 and mailed Dec. 11, 2003 (4 pages).

*Primary Examiner*—Eduardo C Robert
*Assistant Examiner*—David Comstock
(74) *Attorney, Agent, or Firm*—Kauth, Pomeroy, Peck & Bailey LLP

(57) ABSTRACT

A method, system and apparatus for stabilizing a facet joint are provided herein. The surgical method includes angling a screw from a ventral and a lateral side of the spine toward a dorsal and medial side of the spine, and screwing the screw through a superior facet of an inferior vertebra and into an inferior facet of a superior vertebra. The system includes a screwdriver insertable into a surgical opening, a screw coupled to the screwdriver and a torque transmitter coupled to and rotatable with a head on the screwdriver. The screwdriver apparatus includes a handle and a head projecting at an obtuse angle from the handle. The head in turn is coupled to and rotatable with a torque transmitter. The accompanying facet screw includes a sharp and self-tapping point, an ellipsoidal shaft with progressively spaced threads, and a bulbous screw head. The optional cutter includes a narrow, longitudinal shaft with a two-handle closing mechanism.

21 Claims, 5 Drawing Sheets

U.S. PATENT DOCUMENTS

| | | | |
|---|---|---|---|
| 5,397,364 A | 3/1995 | Kozak et al. | |
| 5,451,227 A * | 9/1995 | Michaelson | 606/83 |
| 5,527,312 A | 6/1996 | Ray | |
| 5,549,607 A | 8/1996 | Olson et al. | |
| 5,558,674 A | 9/1996 | Heggeness et al. | |
| 5,569,034 A * | 10/1996 | Meller et al. | 433/105 |
| 5,582,618 A * | 12/1996 | Chin et al. | 606/170 |
| 5,584,831 A | 12/1996 | McKay | |
| 5,611,800 A | 3/1997 | Davis et al. | |
| 5,626,474 A * | 5/1997 | Kukla et al. | 433/141 |
| 5,634,925 A | 6/1997 | Urbanski | |
| 5,702,420 A * | 12/1997 | Sterling et al. | 606/205 |
| 5,716,357 A | 2/1998 | Rogozinski | |
| 5,766,177 A * | 6/1998 | Lucas-Dean et al. | 606/83 |
| 5,927,976 A * | 7/1999 | Wu | 433/82 |
| 5,928,238 A * | 7/1999 | Scarborough et al. | 606/79 |
| 5,947,965 A | 9/1999 | Bryan | |
| 5,984,922 A | 11/1999 | McKay | |
| 6,010,504 A | 1/2000 | Rogozinski | |
| 6,017,343 A | 1/2000 | Rogozinski | |
| 6,019,759 A | 2/2000 | Rogozinski | |
| 6,200,322 B1 | 3/2001 | Branch et al. | |
| 6,251,140 B1 | 6/2001 | Marino et al. | |
| 6,267,761 B1 * | 7/2001 | Ryan | 606/50 |
| 6,287,313 B1 | 9/2001 | Sasso | |
| 6,290,724 B1 | 9/2001 | Marino | |
| 6,336,927 B2 | 1/2002 | Rogozinski | |
| 6,379,354 B1 | 4/2002 | Rogozinski | |
| 6,402,759 B1 * | 6/2002 | Strong et al. | 606/104 |
| 6,409,728 B1 * | 6/2002 | Ehr et al. | 606/51 |
| 6,468,276 B1 | 10/2002 | McKay | |
| 6,485,518 B1 | 11/2002 | Cornwall et al. | |
| 6,540,747 B1 | 4/2003 | Marino | |
| 6,547,795 B2 | 4/2003 | Schneiderman | |
| 6,558,386 B1 | 5/2003 | Cragg | |
| 6,558,387 B2 | 5/2003 | Errico et al. | |
| 6,558,390 B2 | 5/2003 | Cragg | |
| 6,562,046 B2 | 5/2003 | Sasso | |
| 6,575,979 B1 | 6/2003 | Cragg | |
| 6,579,291 B1 | 6/2003 | Keith et al. | |
| 6,582,431 B1 | 6/2003 | Ray | |
| 6,648,893 B2 | 11/2003 | Dudasik | |
| 6,648,915 B2 | 11/2003 | Sazy | |
| 6,669,698 B1 | 12/2003 | Tromanhauser et al. | |
| 6,669,729 B2 | 12/2003 | Chin | |
| 6,689,125 B1 | 2/2004 | Keith et al. | |
| 6,802,844 B2 | 10/2004 | Ferree | |
| 6,805,697 B1 | 10/2004 | Helm et al. | |
| 6,830,574 B2 * | 12/2004 | Heckele et al. | 606/104 |
| 6,899,716 B2 | 5/2005 | Cragg | |
| 6,921,403 B2 | 7/2005 | Cragg et al. | |
| 6,923,814 B1 | 8/2005 | Hildebrand et al. | |
| 2002/0123751 A1 * | 9/2002 | Fallin | 606/73 |
| 2004/0147936 A1 * | 7/2004 | Rosenberg et al. | 606/99 |
| 2004/0254605 A1 * | 12/2004 | DiFrancesco et al. | 606/205 |

* cited by examiner

METHOD AND APPARATUS FOR STABILIZATION OF FACET JOINT

BACKGROUND

As the lumbar spine ages, disc degeneration occurs. This degeneration causes a reduction in the vertical height of the disc, and a diminution of its viscoelastic properties. The profile of the spine also changes with age. The swayback curvature of youth becomes the flat-back of old age. As a result, arthritic changes occur in the facet joints due to the increased biomechanical stress on the posterior side of the spine.

With a recent increased understanding in the biomechanics of the spine, it is acknowledged that maintenance of the normal curvature of the lumbar spine is preferable. For example, it is now known that the instantaneous center of rotation in the lumbar spine is 7 mm or 8 mm anterior to the posterior edge of the vertebral body, and it is approximately 2 cm anterior to the posterior elements and the facet joints. These joints are arranged in a cross-sectional "J" shape, and are designed to stabilize the spine and transmit the biomechanical forces from one vertebra to another.

These joints are an integral part of the stability of the motion segment. The facet joints transmit torsional force, facilitating normal gait. So, when spinal fusions are considered, it is important to re-establish the normal biomechanical arrangement, and to restore the sagittal profile of the spine to obtain optimal results. Arthritic changes in the facet joints following disc degeneration can cause mechanical back paint. If they become excessive, these arthritic changes can cause spinal stenosis.

Historically, some of the first attempts to attain spinal fusion, or spinal arthrodesis, utilized a method whereby the facet joints were stabilized by fusion. Fusion of the motion segment entails removal of the cartilage from the facet joint, and then packing bone into this joint to obtain immobility. In so doing, forces were transmitted from one segment to the next by a bony connection rather than by a flexible connection.

Another prior art method of stabilizing the facet joint is shown in FIG. 1. In this method, a screw was inserted from a dorsal and medial approach, through the facet joint, running from the medial to lateral side of the spine. The screw passed through the inferior facet of the vertebra above, and as it crossed the joint, it penetrated the superior facet of the vertebra below. However, this original technique is flawed in that the surgeon is unable to visualize where the tip of the screw comes to rest. The greatest complication of this technique is that the tip of the screw can end up in the vicinity of the exiting segmental nerve root. Nerve root encroachment can, in turn, produce serious radicular pain, which is the major complication of this original method. Accordingly, a need exists for a method of stabilizing facet joints which improves the safety of the stabilizing screw.

SUMMARY

The current invention is directed to a method, system, and apparatus for stabilizing a facet joint. One embodiment of a method according to the current invention includes angling a screw from a substantially lateral side of the spine toward a dorsal and medial side of the spine and screwing the screw through a superior facet of an inferior vertebra and into an inferior facet of a superior vertebra.

In another embodiment, the screw continues to travel through the inferior facet of the superior vertebra and into a spinous process of the same superior vertebra.

In yet another embodiment, the inserting also includes providing a screwdriver coupled to the screw by an attachment end, and the screwing also includes uncoupling the screwdriver to the screw.

One embodiment of a system according to the present invention includes a screwdriver insertable into a surgical opening, a screw coupled to the screwdriver and a torque transmitter. The screwdriver in this embodiment may include a head, which is coupled to a handle and the torque transmitter. In this embodiment, the head is rotatable about an axis in response to the torque transmitted by the torque transmitter, which is rotatable about another axis. In such an embodiment the screw rotates with the head about the same axis.

In another embodiment, the screw and an attachment end of the head are formed in one piece. In still another embodiment, the screw is grasped by the head.

In yet another embodiment, the screwdriver according to the invention includes a head projecting from the handle at an angle between 75 degrees and 120 degrees.

In still yet another embodiment, the screwdriver includes a dial located rotatable on the handle and coupled to the torque transmitter to transmit torque from the dial rotation to the head.

In still yet another embodiment, the screwdriver includes a stationary section between the handle and the head, where the handle is rotatable and coupled to the torque transmitter to transmit torque to the head.

In still yet another embodiment, the torque transmitter is electrically coupled to a motor to transmit torque to the head.

In one embodiment of a facet screw according to the invention, the screw includes a screw head portion, a point portion and a shaft portion. In this embodiment, the shaft portion is substantially elliptical in shape and has threads that are spaced from each other at progressively greater distances on the end of the shaft portion closer to the screw head. In one embodiment, the screw can be formed wholly or partially of bioactive or bioabsorbable materials.

In one embodiment of a cutter for cutting a facet screw away from a facet screwdriver within a surgical opening according to the invention, the cutter includes a first and second handle rotatably connected and a longitudinal shaft extending from the first handle. In this embodiment, the longitudinal shaft is sufficiently narrow to allow viewing of the screw while both the screwdriver and cutter are within the surgical opening. The longitudinal shaft includes a first and second cutting edge which project at an angle from the shaft and are connected to the first and second handles such that when the handles are squeezed together, the cutting edges move closer to each other.

In another embodiment of a cutter, the first and second handles can be substituted with a ratchet mechanism rotatably coupled to the first and second cutting edges, such that when a activating end of the ratchet mechanism is rotated, the cutting edges move closer to each other.

In still another embodiment, the cutting edges project substantially orthogonal to the shaft and the first handle. Additionally, in yet another embodiment, at least one of the cutting edges includes carbide.

BRIEF DESCRIPTION OF THE DRAWINGS

These and other features and advantages of the present invention will be better understood by reference to the following detailed description when considered in conjunction with the accompanying drawings where.

DETAILED DESCRIPTION

Figure 1:
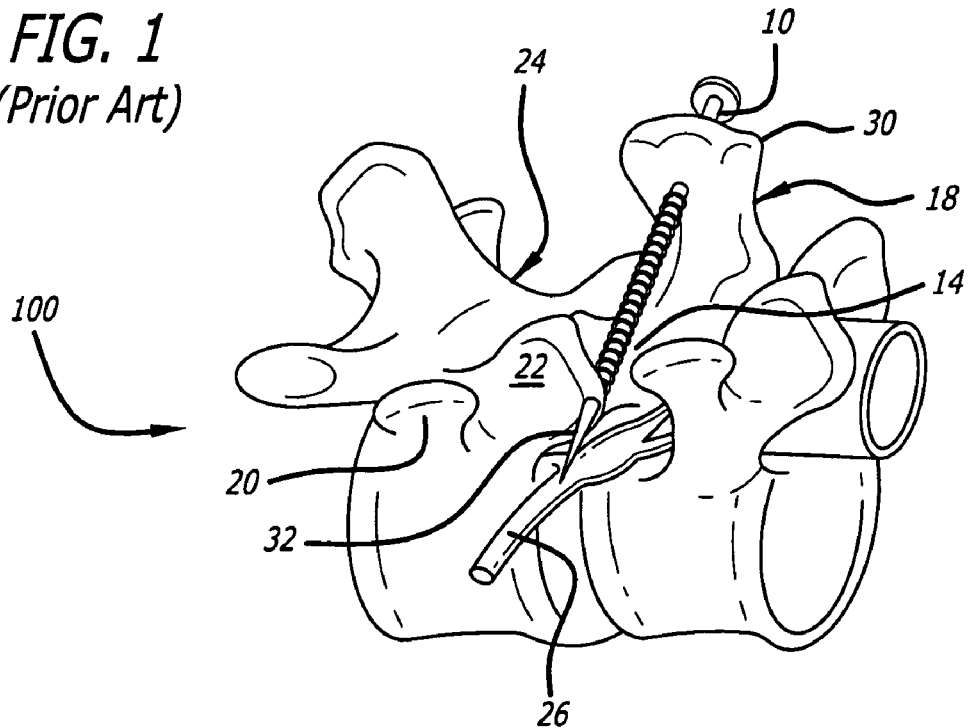
FIG. 1 is a side perspective view of a prior art facet joint fixation system.

The present invention is directed to a method, system, and apparatus for stabilizing a facet joint in a spine. FIG. 1 shows a prior art facet joint stabilization system. In this system, a screw 10 is inserted from the dorsal and medial sides of a spine 100 into facet joint 12 toward the ventral and lateral sides of the spine 100. The screw 10 passes through the spinous process 30 to the inferior facet 14 of superior vertebra 18 and into the base of the superior facet 22 of the immediately inferior vertebra 24 pointing towards the transverse process 20.

Nerve 26 exits from the spine 100 through neural foramen 28. The spinous process 30 largely blocks the view of the exiting nerve 26 from the dorsal side. Because the surgeon's view of both the tip 32 of the screw 10 and the exiting nerve 26 is blocked, if the screw 10 is angled at even a slightly incorrect angle, the tip 32 of the screw 10 can hit the exiting nerve 26.

Figure 2:
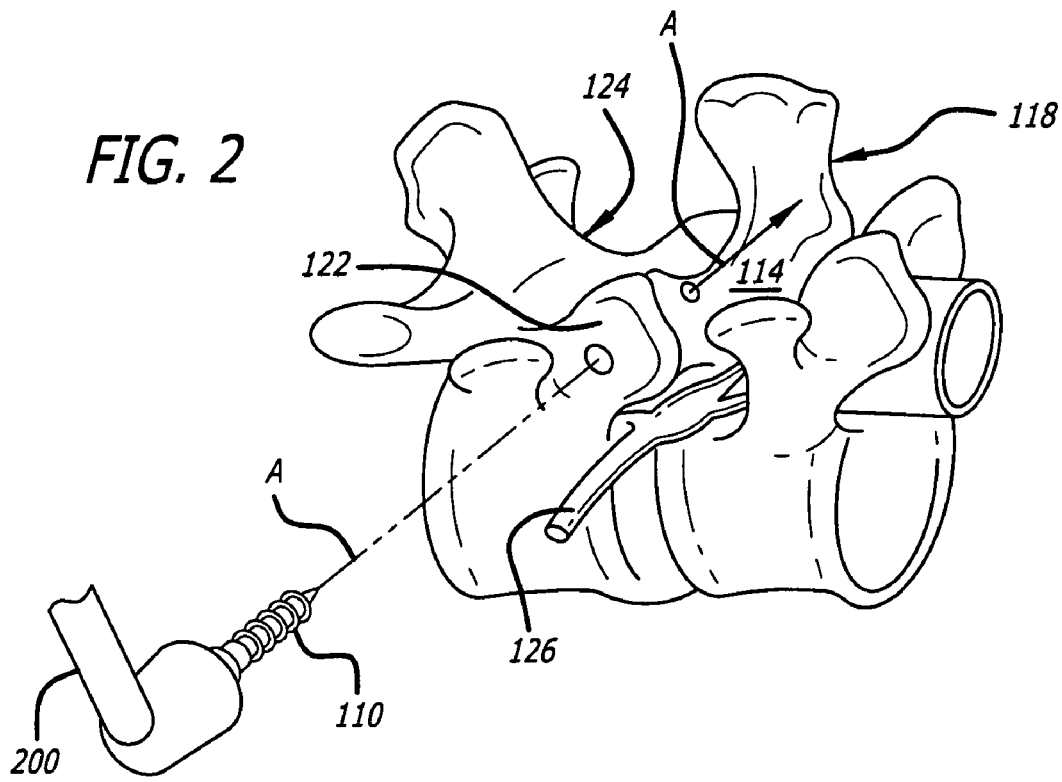
FIG. 2 is a side perspective view of one embodiment of a system according to the invention.

In contrast to the system shown in FIG. 1, FIG. 2 shows one embodiment of the facet joint stabilization system and method of the present invention. In the method shown in FIG. 2, an angulated screwdriver 200 and screw 110 are inserted into a posterolateral surgical opening (not shown). The angulated screwdriver 200 then inserts the screw 110 into the base of the superior facet 122 of the inferior vertebra 124. The angle of insertion is from the slightly ventral and substantially lateral ("inferolateral") sides of spine 100 towards the dorsal and medial ("dorsomedial") sides of the spine 100. The screw 110 then passes through the inferior facet 114 of the immediately superior vertebra 118. As the screw is inserted, the exiting nerve 126 is in plain sight, so the surgeon is better able to avoid encroaching on the nerve 126 with the screw 110.

Although an angulated screwdriver is shown in FIG. 2, it should be understood that any device suitable for inserting screws into a patient as described above may be utilized with the method according to the present invention.

One embodiment of the angulated screwdriver 200 is shown in more detail in FIGS. 3a-3d. In the embodiment shown in FIG. 3a, The screwdriver 200 has a handle 202 and a head 204. For purposes of this disclosure, a "handle" is a graspable shaft, and a "head" is the projecting end portion of the screwdriver. The head 204 can extend at an angle of between 0 and 100 degrees from the axis of the handle 202. In one embodiment, the head is angled at between 70 and 80 degrees from the axis of the handle 202, so that the head and the handle form an obtuse angle. In another embodiment, the angle of the head 204 is adjustable. The head 204 in the embodiment shown in FIG. 3a includes an attachment end 205 configured to mate with screw head 220 of screw 110. The head 204 is rotatable about its angled axis.

Figure 3A:
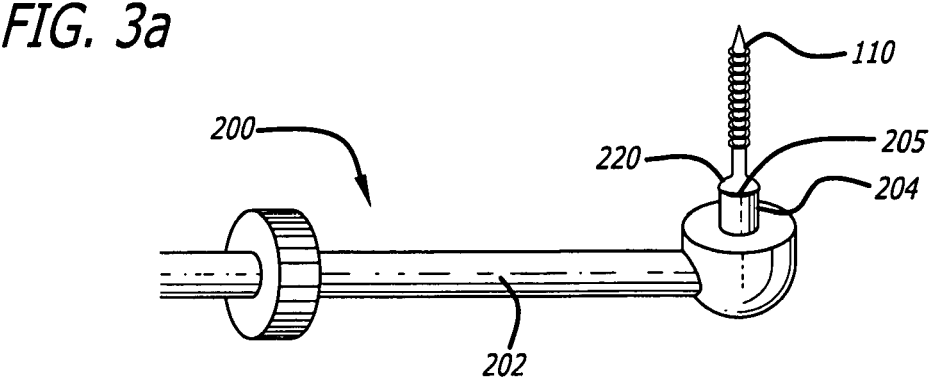
FIG. 3a is side view of one embodiment of a screwdriver and a screw system according to the invention.
Figure 3B:
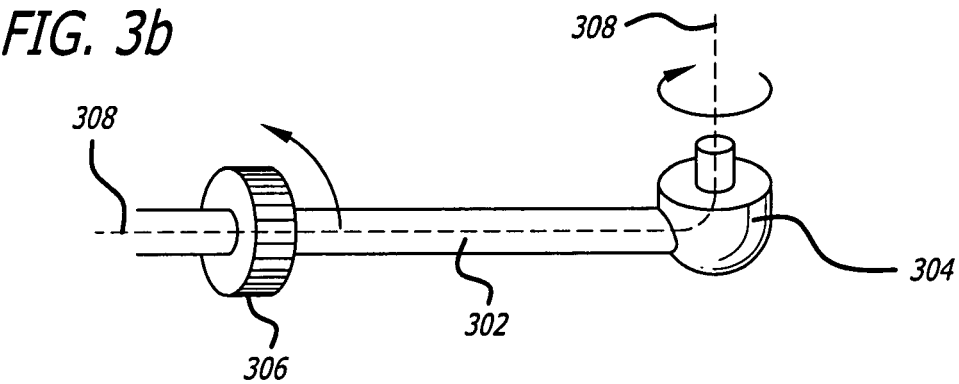
FIG. 3b is a side view of another embodiment of a screwdriver according to the invention.

In the embodiment shown in FIG. 3b, the head 304 is coupled to a dial 306 at one end of the handle 302 by a bent axis 308, such that when the dial 306 is turned relative to the handle 302, the head 304 axially rotates with the dial 306. The bent axis 308 can be any material capable of transmitting torque from the dial 306 to the head 304. In one embodiment, the bent axis 308 is a braided cable, such as is used with a Bowden speedometer.

Although a dial is used to generate torque in the head of the embodiment shown in FIG. 3b, any suitable mechanism may be used. For example, in the embodiment shown in FIG. 3c, a stationary section 410 is coupled between the head 404 and the handle 402, and the head 404 and handle 402 are coupled along bent axis 408 such that the head 404 rotates about its axis 408 when the handle 402 is rotated about its axis 408.

Figure 3C:
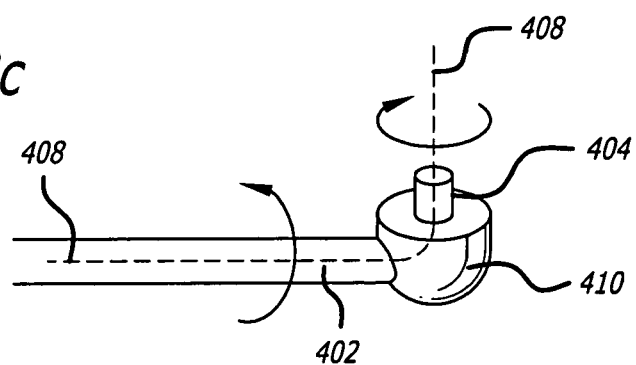
FIG. 3c is a side view of yet another embodiment of a screwdriver according to the invention.
Figure 3D:
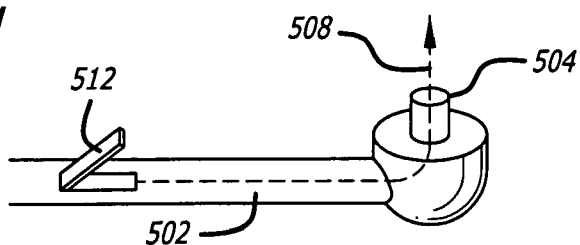
FIG. 3d is a side view of another embodiment of a screwdriver according to the invention.

Further, although any manually moved mechanisms are shown in FIGS. 3a-3c, in the embodiment shown in FIG. 3d, the head 504 is coupled to a motor 505, which rotates the head 504 about its angled axis 508 and is activated by a switch 512 on the handle 502. Although several torque transmitting devices are described above, one skilled in the art will recognize other suitable means for rotating the head about its angled axis, such systems are intended to be included in the present invention.

Figure 4A:
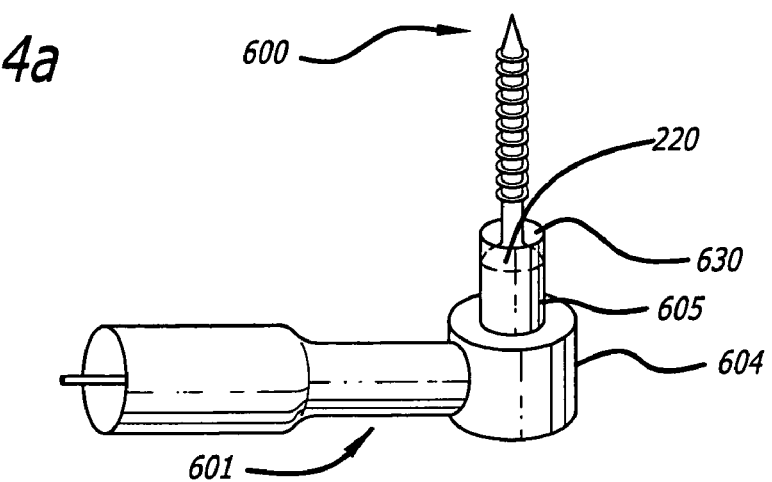
FIG. 4a is a side view of an embodiment of a screwdriver and facet screw system according to the invention.
Figure 4B:
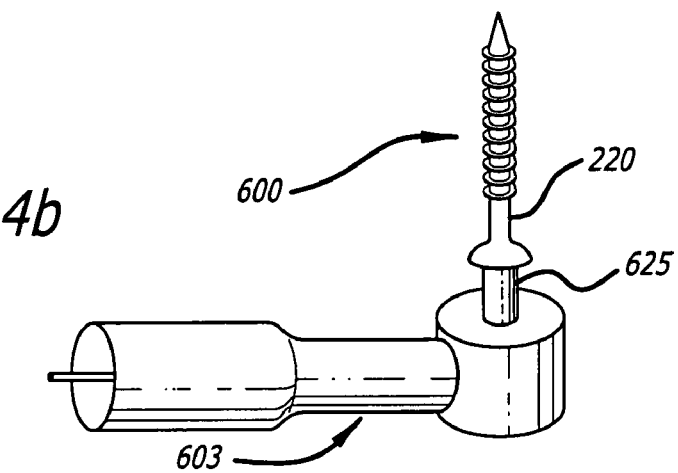
FIG. 4b is a side view of another embodiment of a screwdriver and facet screw system according to the invention.
Figure 4C:
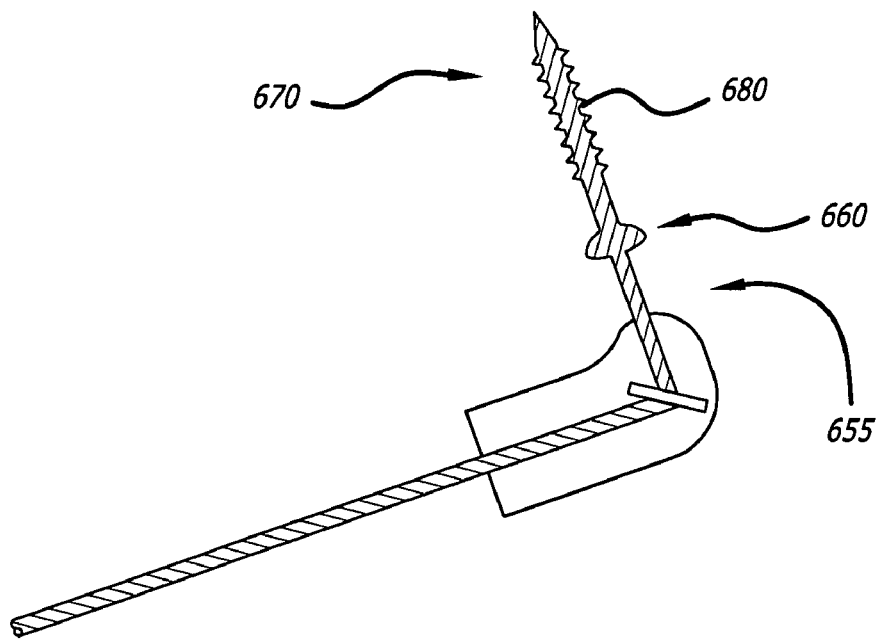
FIG. 4c is a side view of another embodiment of a system according to the invention where the facet screw and a screw head of the screwdriver are formed in one piece.

One exemplary embodiment of the screwdriver 200 where the screw is coupled to the screwdriver, discussed in relation to FIG. 3a, is shown in more detail in FIGS. 4a-4c. In the embodiment shown in FIG. 4a, the head 604 can be secured to the screw head 220 by a basket 605. The basket 605 includes a circumferential edge 630, which circumferentially surrounds and holds the screw head 220 securely to the screwdriver 601 through frictional forces or biasing means for example. In this embodiment, once the screw 600 is drilled into the facet joint (not shown), the retaining forces can be overcome by wiggling or popping the basket 605 away from the screw head 220 to allow the screwdriver 601 to be removed from the surgical opening (not shown).

In another embodiment shown in FIG. 4b, the attachment end 625 of the screwdriver 603 removably engages an opening (not shown) in the screw head 220, and when the screw 600 is fixed in the facet joint, the attachment end 625 can be snapped away from the screw 600 to allow the screwdriver 603 to be removed from the surgical opening.

In the embodiment shown in FIG. 4c, the attachment end 655 is formed in one piece with the screw head 660. After fixation of the screw 670 in the facet joint, the screw shaft 680 can be cut or snapped off from the screw head 660, or the attachment end 655 can be cut or snapped off from the screw head 660 by a cutter (shown in FIGS. 6a and 6b). In one embodiment, the screw can be snapped off with a torque of around 25-30 Newtons.

It is also within the scope of the invention to attach the screw to the attachment end by any other suitable means, such as through an adhesive, magnetic coupling, flange, clamp, etc., that is capable of holding the screw head onto the attachment end until it is secured in the facet joint. For example, FIG. 4d shows an embodiment of the screw driver in which a simple biasing clamp is used to secure the screw to the driver.

Figure 5:
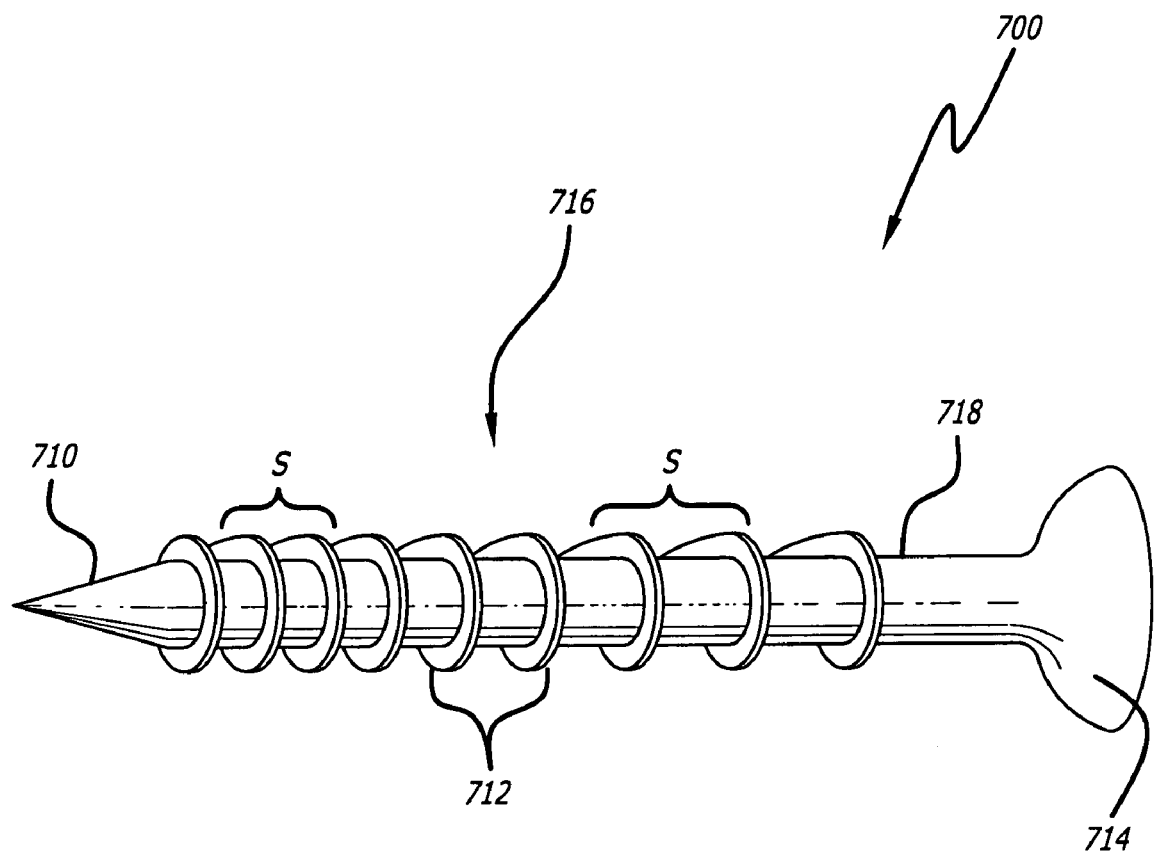
FIG. 5 is a side view of an embodiment of a facet screw according to the invention.

Although any screw can be used with the screwdriver of the present invention, one preferred embodiment is shown in more detail in FIG. 5. The screw 700 of this embodiment has a sharp point 710, which can dig into the bone and minimize skidding. In one embodiment, the screw is around 10-14 mm in length. The sharp point 710 is preferably self-tapping, so the passage through the facet joint does not have to be drilled. The screw 700 has a substantially ellipsoidal shaft 716, which narrows toward the point 710 and shank 718. The ellipsoidal shape allows the screw head 714 to compress onto the bone. In one embodiment, the shaft is around 2 mm in diameter. The spacings "s" between the threads 712 of this embodiment become progressively wider toward the screw head 714 of the screw 700 and project at a substantially perpendicular angle outward from the shaft 716.

The screw head 714 in this embodiment is substantially round and bulbous, to allow the screw head 714 to project slightly from the bone. This projection would simplify removal through muscle or cutting of the screw 700. As this embodiment of the screw 700 is inserted into and compresses the bone, a screwdriver removably fixed to the screw head 714 can be simply pulled away from the screw 700 and removed from the surgical opening, leaving the screw 700 embedded in the bone. In one embodiment, the screw is wholly or partially formed of bioactive or bioabsorbable material.

Figure 6:
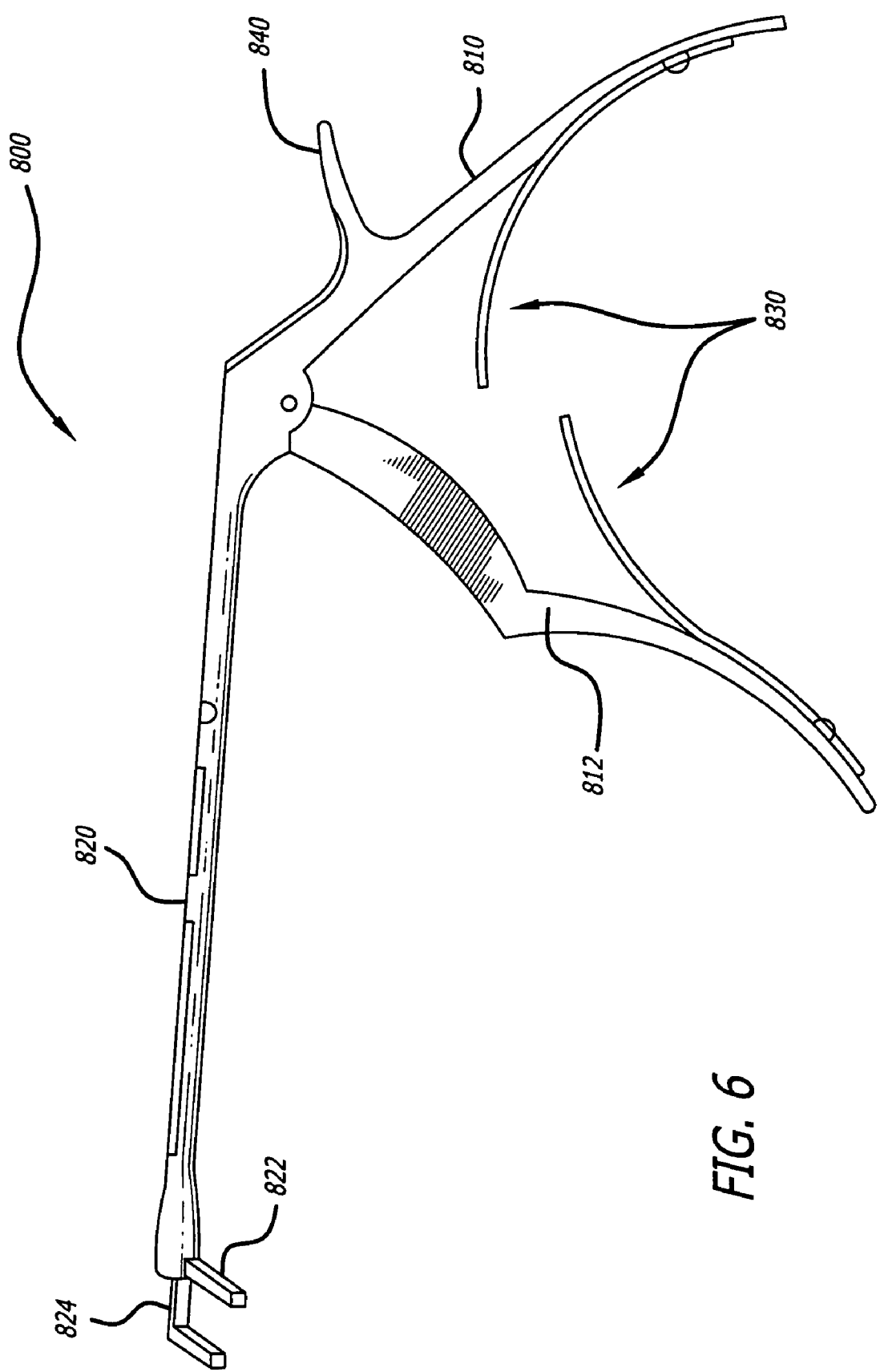
FIG. 6 is a side view of an embodiment of a cutter according to the invention.

One exemplary embodiment of a cutter, which may optionally be used in conjunction with the screwdriver system shown in FIG. 4c, is shown in FIG. 6. The cutter 800 includes a first and a second handle 810, 812, and a long, narrow shaft 820 with first and second cutting edges 822 and 824 projecting parallel to each other from its free end. In this embodiment, the cutting edges 822 and 824 project substantially orthogonally from the first handle 810 and the shaft 820. Although a substantially orthogonal angle is likely more intuitive for a surgeon, any other angle of projection is also within the scope of this invention.

In one embodiment, the first and second cutting edges 820 and 822 contain carbide, but one skilled in the art will recognize that any material of sufficient strength to cut the attachment end or the narrow shaft of the screw will also be within the scope of this invention.

The first handle 810 is hinged to the second handle 812 and is integral with the shaft 820 and the first cutting edge 822. The second handle 812 is coupled to the second cutting edge 824 such that when the second handle 812 is squeezed toward the first handle 810, the second handle 812 pulls the second cutting edge 824 toward the first cutting edge 822. When the first and second cutting edges 822 and 824 surround the attachment end of the screwdriver or the narrow shank, the attachment end or shank can be cut, allowing the screwdriver to be removed from the surgical opening.

A spring 830 can be added to cause the handles 810 and 812 to spring away from each other when the handles 810 and 812 are not squeezed together. Although the embodiment shown in FIG. 6a depicts the spring 830 as two elastic, curved strips, any spring which counters a squeezing force can be used. A grip stabilizer 840 can also be added to the first handle 810 to assist the surgeon in squeezing the handles together. Alternatively, if a surgeon lacks sufficient hand strength to use the previous embodiment, a ratchet closure mechanism 811 can replace the first and second handles 810 and 812 and spring 830 to allow a surgeon to tighten the first and second cutting edges 820 and 822.

Preferably, the shaft 820 is narrow enough to insert into an approximately 1.5" diameter posterolateral surgical opening, which already contains the screwdriver, and allow enough light into the opening for the surgeon to see around it to the attachment end of the screwdriver or the narrow shank of the screw. The shaft 820 is also preferably long enough to reach the attachment end or the shank.

Although specific embodiments are disclosed herein, it is expected that persons skilled in the art can and will design alternate instruments and methods that are within the scope of the following claims either literally or under the Doctrine of Equivalents.

What is claimed is:

1. A system for stabilizing a facet joint comprising:
    a screwdriver, itself comprising:
        an elongated shaft having proximal and distal ends and defining a first axis;
        a torque generator disposed at the proximal end of the shaft;
        a torque projecting head disposed at the distal end of the shaft and defining and rotatable about a second axis, wherein the first and the second axes are defined by a fixed angle therebetween;
        a torque transmitter coupled between the torque generator and the torque projecting head, such that rotation of the torque generator about the first axis rotates the torque projecting head about the second axis;
        a self-tapping screw defining a screw head and a threaded screw shaft, the screw being integrally formed as a single piece with the torque projecting head of the screwdriver; and
    wherein the screwdriver is sized to be insertable into a posterolateral surgical opening,
    and the screw is sized to be insertable into said facet joint.

2. The system for stabilizing according to claim 1, further comprising a cutter with a longitudinal shaft and a first and second cutting edge, the longitudinal shaft configured to reach one of the screw and the torque projecting head through a surgical opening and sufficiently narrow to allow a view of the screw through the surgical opening.

3. The system for stabilizing according to claim 2, wherein the cutter further comprises:
    a first handle;
    a second handle rotatably connected to the first handle, wherein the longitudinal shaft extends from the first handle with a diameter sufficiently narrow to allow a view of said facet screw through said surgical opening when the longitudinal shaft is inserted into said surgical opening; and
    wherein the first cutting edge is fixedly coupled to the first handle and projects from the longitudinal shaft at a first angle, and wherein the second cutting edge is coupled to the second handle and projects parallel to the first cutting edge such that when the second handle is moved closer to the first handle the second cutting edge approaches a facing edge of the first cutting edge.

4. The system for stabilizing according to claim 3, wherein the first angle is substantially orthogonal to the first handle and the longitudinal shaft.

5. The system for stabilizing according to claim 3, wherein the at least one of the first cutting edge and the second cutting edge comprises carbide.

6. The system for stabilizing according to claim 3, wherein the first handle includes a grip stabilizer.

7. The system for stabilizing according to claim 2, wherein the longitudinal shaft, has a first end and a second end, with a diameter sufficiently narrow to allow a view of said facet screw through said surgical opening when the longitudinal shaft is inserted into said surgical opening, wherein the first cutting edge is fixedly coupled to the first end and projects from the longitudinal shaft at a first angle, and wherein the second cutting edge is coupled to the first end and projects parallel to the first cutting edge; and wherein the cutter further comprises a ratchet mechanism, having an activating end proximate to the second end and rotatably coupled to the first and second cutting edges, such that when the activating end is rotated relative to the first and second cutting edges, the second cutting edge approaches a facing edge of the first cutting edge.

8. The system for stabilizing according to claim 7, wherein the first angle is substantially orthogonal to the longitudinal shaft.

9. The system for stabilizing according to claim 7, wherein the at least one of the first cutting edge and the second cutting edge comprises carbide.

10. The system for stabilizing according to claim 1, wherein the torque transmitter is a cable.

11. The system for stabilizing according to claim 10, wherein the cable is braided.

12. The system for stabilizing according to claim 1, wherein the fixed angle is obtuse.

13. The system for stabilizing according to claim 1, wherein the fixed angle is approximately 90-120 degrees.

14. The system for stabilizing according to claim 1, wherein the fixed angle is adjustable.

15. The system for stabilizing according to claim 1, wherein the torque generator further comprises a motor electrically coupled to the torque transmitter for rotating the torque transmitter about the first axis.

16. The system for stabilizing according to claim 1 wherein the screw for fixing a facet joint,
    wherein the threads of the threaded shaft are spaced from each other at a progressively larger distance towards the screw head portion, and
    wherein the threaded shaft is substantially elliptical.

17. The system for stabilizing according to claim 16, wherein the screw head portion is substantially bulbous.

18. The system for stabilizing according to claim 16, wherein a total length of the screw is approximately 10-14 mm.

19. The system for stabilizing according to claim 16, wherein a diameter of the threaded shaft portion of the screw is approximately 2 mm.

20. The system for stabilizing according to claim 16, wherein the screw comprises a bioactive material.

21. The system for stabilizing according to claim 16, wherein the screw comprises a bioabsorbable material.

* * * * *